United States Patent
Hasegawa

(10) Patent No.: US 7,160,249 B2
(45) Date of Patent: Jan. 9, 2007

(54) ENDOSCOPE IMAGE PICKUP UNIT FOR PICKING UP MAGNIFIED IMAGES OF AN OBJECT, A FOCUS ADJUSTMENT APPARATUS AND METHOD, AND A FOCUS RANGE CHECK APPARATUS AND METHOD FOR THE SAME

(75) Inventor: Naoki Hasegawa, Chofu (JP)

(73) Assignee: Olympus Corporation, Tokyo (JP)

( * ) Notice: Subject to any disclaimer, the term of this patent is extended or adjusted under 35 U.S.C. 154(b) by 162 days.

(21) Appl. No.: 10/808,297

(22) Filed: Mar. 25, 2004

(65) Prior Publication Data

US 2004/0190159 A1 Sep. 30, 2004

(30) Foreign Application Priority Data

Mar. 28, 2003 (JP) ............................. 2003-091080

(51) Int. Cl.
*A61B 1/04* (2006.01)
*A61B 1/06* (2006.01)
(52) U.S. Cl. ...................................... 600/167; 600/129
(58) Field of Classification Search ................ 600/163, 600/167, 168, 176, 129; 359/738–740
See application file for complete search history.

(56) References Cited

U.S. PATENT DOCUMENTS

| 2,730,016 | A | * | 1/1956 | Bertele | ........................ 359/740 |
| 4,189,211 | A | * | 2/1980 | Taylor | ......................... 359/663 |
| 5,644,435 | A | * | 7/1997 | Shikama | ...................... 359/691 |
| 5,717,527 | A | * | 2/1998 | Shibayama | .................. 359/690 |
| 5,930,051 | A | * | 7/1999 | Sato | ............................ 359/690 |
| 6,069,651 | A | * | 5/2000 | Tsuyuki et al. | ................ 348/75 |
| 2005/0054901 | A1 | * | 3/2005 | Yoshino | ...................... 600/176 |

* cited by examiner

*Primary Examiner*—John Leubecker
*Assistant Examiner*—Philip R Smith
(74) *Attorney, Agent, or Firm*—Arnold International; Bruce Y. Arnold

(57) ABSTRACT

An endoscope image pickup unit is disclosed that captures magnified images of an object. An objective optical system of the image pickup unit includes, in order from the object side, a front lens group having positive refractive power and an aperture stop. Various conditions are satisfied so as to provide an observation scale factor in the range of about 200 to 2000 so that cellular details can be observed, as in a microscope, while keeping the objective optical system sufficiently compact for insertion within a patient. Also disclosed is a focus adjustment apparatus and method for the endoscope image pickup unit, and a focus range check apparatus and method for the endoscope image pickup unit.

2 Claims, 8 Drawing Sheets

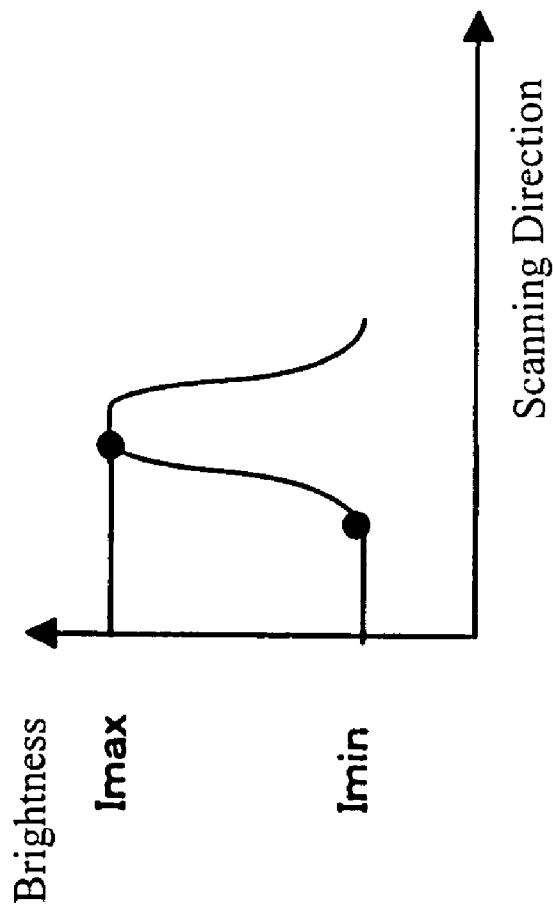
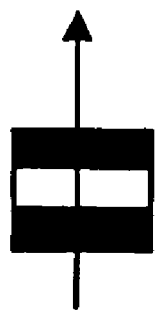
Fig. 3(b)
Fig. 3(a)

ENDOSCOPE IMAGE PICKUP UNIT FOR PICKING UP MAGNIFIED IMAGES OF AN OBJECT, A FOCUS ADJUSTMENT APPARATUS AND METHOD, AND A FOCUS RANGE CHECK APPARATUS AND METHOD FOR THE SAME

CROSS REFERENCE TO RELATED APPLICATION

This application claims the benefit of foreign priority from Japanese Patent Application No. 2003-091080, filed Mar. 28, 2003, the contents of which are hereby incorporated by reference.

BACKGROUND OF THE INVENTION

Conventional endoscopes have a large field angle between 90° and 140° so that tissues inside the body can be observed without overlooking lesions, and they change the distance to the object in order to obtain enlarged or reduced images of an object to be observed. Thus, they are designed so as to have a large depth of field so that objects at a distance between 3 mm and 50 mm can be observed without focus adjustment, and they have an observation scale factor of approximately 30 to 50 when viewed on a 14 inch monitor screen, which is sufficient to observe diseased tissues.

In order to obtain additional magnification, zoom optical systems have been used with conventional endoscopes. The largest observation scale factor obtained with zoom optical systems is approximately 70 when viewed on a 14 inch monitor screen. The zoom optical system has a built-in zoom lens driving mechanism, and as a result, the endoscope has an insert tip with an outer diameter greater than 10 mm and requires complex operations. Such an endoscope has limited applications.

When an abnormality is difficult to diagnose by observation of tissue images, such as when a lesion is very small, suspicious tissues are generally excised using a therapeutic instrument in the course of an endoscopic observation. The excised tissues are then examined under a microscope.

An endoscope uses incident light illumination from an illumination optical system that is positioned around the objective optical system. A microscope uses an objective optical system and an illumination optical system that usually are positioned on opposite sides of the sample, with the sample usually being illuminated from the back (i.e., transmission light illumination is usually used). The sample will have been previously appropriately processed for observation. For example, it will have been thinly sliced so that it transmits light well. Often, the sample also will have been stained so as to provide images having improved contrast.

Laser-scanning-type, confocal endoscopes have been proposed that can be inserted into a living body and which have resolutions sufficient for cellular observation. There exist confocal optical systems which have a pinhole that passes light in an Airy disc light pattern, with the pinhole being positioned at a conjugate position to the image plane. Such optical systems acquire information of a diffraction-limited level for each point of an object surface in a field of view. A laser beam from an illumination optical system scans the object, and information obtained from light reflected by each point of the object surface is combined so as to produce an image representing either two-dimensional or three-dimensional information. Where three-dimensional information is obtained, high resolution is realized not only within a planar surface but also in the depth direction.

Conventional endoscopes require a wide field of view and have an image pickup unit that includes an image pickup element and ah objective optical system having an image scale factor smaller than unity. Thus, object images are formed onto the image pickup surface of the image pickup unit in reduced size. Further, in order to assure an appropriate depth of field for observation, conventional endoscopes require a positional adjustment during assembly of the image pickup unit in which the image pickup surface of the image pickup element is fixed near the image plane of the objective optical system.

FIG. 1 shows the range of focus on the object side and on the image side for a conventional endoscope. In a conventional endoscope, the objective optical system projects the relative positional change between the object and the object-side leading surface of the objective optical system onto the image side at a reduced size. Therefore, it is somewhat difficult to find the best in-focus position since a small deviation from the best in-focus position corresponds to a large difference in object position that causes a de-focused state. In order to avoid this difficulty, the adjustment method illustrated in FIG. 1 is conventionally used. FIG. 1 shows the upper and lower limits ZoA and ZoB, respectively, in object space of an optical system having a desired depth of field (for example, at distances of 3 mm and 50 mm from the object-side leading surface of the objective optical system). The two corresponding images ZmA, ZmB are then formed as illustrated in reduced size and spacing. The mean position between the image-space positions ZmA and ZmB is determined, and the image pickup surface of the image pickup element is moved along the optical axis of the objective optical system in order to coincide with this mean position so as to achieve the optimum in-focus adjustment.

For a conventional endoscope, the image of an object will be formed by the objective optical system onto the image pickup surface of the image pickup element in reduced size even when the object is inclined relative to the objective optical system. Therefore, even when the object is inclined relative to the objective optical system, images on the image pickup surface will not be significantly asymmetric near the periphery of the field of view, and the captured image will not be subject to excessively unbalanced image aberrations. Thus, for focus adjustment of the image pickup unit of a conventional endoscope, excellent images can be obtained simply by ensuring mechanical accuracy of the focus adjustment apparatus.

On the other hand, a microscope has an objective optical system with an image scale factor having an absolute value greater than unity so as to form an image of an object that is enlarged in size. This also results in the depth of field on the object side being projected into image space with magnification. Therefore when focusing, a microscope commonly moves the stage on which the object is fixed rather than changing the position at which the image is observed.

As mentioned above, an objective optical system having an image scale factor with an absolute value greater than unity projects the relative positional change between the object and the object-side leading surface of the objective optical system onto the image side with magnification. Therefore, even when the image pickup surface of the image pickup element is positioned at the image plane of the objective optical system, the image on the image pickup surface will be significantly asymmetric near the periphery of the field of view when an object has its surface normal substantially inclined to the optical axis of the objective optical system. Such inclination causes the object surface to occupy significant depth in object space and causes adverse effects on the picked-up image with regard to balance of the aberrations. Thus, a sample for observation must be properly oriented on the microscope stage and the microscope stage on which the sample is fixed must be precisely adjusted relative to the objective optical system.

For the conventional way in which living tissues are removed and examined ex vivo, it takes from several days to several weeks to identity abnormal tissues. In addition, the cell sample that is isolated and fixed to be observed is only a tiny part of a removed tissue. Thus, although conventional ex vivo observation provides information on cellular structures, no functional information such as the fluid circulation within cells is provided because the circumstances are completely different from those of in vivo examination.

A small-sized image pickup unit with an objective optical system having a large scale factor comparable to that of a microscope and which has a high resolution is necessary in order to form clear cellular images of a lesion within a living body. The objective optical system used in conventional endoscopes does not meet such requirements. The objective optical system used in microscopes is satisfactory in performance, but is too large in diameter for insertion into a living body. Heretofore, no image pickup unit has been proposed that meets the above-discussed requirements. Laser-scanning-type, confocal endoscopes have a problem in that, at their present state of development, their scanning speed is too slow for providing in vivo, real-time observations. In addition, within a living body, an object cannot be fixed in a position where the objective optical system is accurately focused, as is possible when observing an excised sample using a microscope. Therefore, with the image pickup units, the image pickup surface of the image pickup element should be pre-adjusted to a fixed position that is suitable for in vivo cellular observation.

When image pickup units as discussed above are focused in the same manner as with a conventional endoscope, the following problems arise.

1) The objective optical system will have a significantly smaller depth of field and the relative positional change between the object and the object-side surface of the objective optical system will be projected onto the image side so as to be magnified in size. Thus, in order to adjust the position of the image pickup surface accurately, it is necessary to place the object used for focus adjustment with a precision and accuracy smaller than a micron (i.e., in submicrons). This makes the focus adjustment difficult to reproduce consistently.

2) Although positioned within the mechanical accuracy of the focus adjustment apparatus, if an object surface is oriented so that its surface normal is significantly inclined to the optical axis of the objective optical system, the image on the image pickup surface of the image pickup element will be asymmetric near the periphery of the field of view, causing noticeable adverse effects on the captured images (i.e., the asymmetry itself causes the adverse effects).

3) An endoscope that is designed for use with its object-side surface of the objective optical system in contact with the object for observation has the near point of the depth of field at the objective optical system. Therefore, no object for focus adjustment can be placed at the near point of the depth of field.

Thus, a new focus adjustment method and a new focus range checking method are needed for magnifying endoscopes that allow in vivo, real-time, magnified observation of intact living cells.

BRIEF SUMMARY OF THE INVENTION

The present invention relates to an image pickup unit that captures magnified images for in vivo observation, and in particular relates to a magnifying image pickup unit having a scale factor suitable for cellular observation, a focus adjustment method and apparatus for the magnifying image pickup unit, and a focus range check method and apparatus for the magnifying image pickup unit. The purposes of the present invention are to provide an image pickup unit that realizes in vivo, real-time cellular observation, to provide a focus adjustment method and apparatus for the image pickup unit, and to provide a focus range check method and apparatus for the image pickup unit.

BRIEF DESCRIPTION OF THE DRAWINGS

The present invention will become more fully understood from the detailed description given below and the accompanying drawings, which are given by way of illustration only and thus are not limitative of the present invention, wherein:

FIG. 3(a) illustrates a contrast chart object having an alternate black/white band pattern, and FIG. 3(b) shows the image signals that are obtained from an image pickup element after scanning such an object in the direction indicated by the arrow in FIG. 3(a);

DETAILED DESCRIPTION

Figure 1:
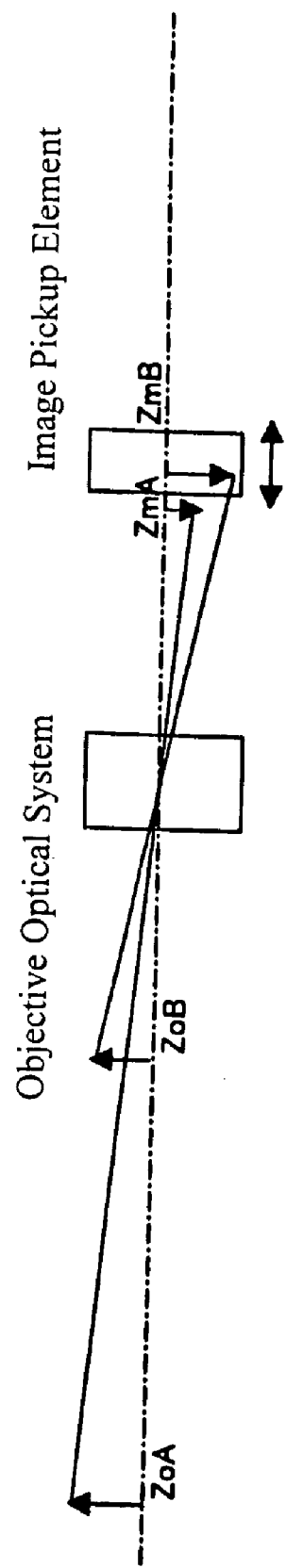
FIG. 1 is a block diagram of an objective optical system and image pickup element for illustrating focus adjustment in a conventional endoscope.

The image pickup unit of the present invention includes an endoscope image pickup unit that is provided with an objective optical system that forms magnified images (i.e., has an image scale factor with an absolute value greater than unity) wherein the objective optical system includes, in order from the object side, a front lens group having positive refractive power and an aperture stop. The following conditions are preferably satisfied:

$$0.9 \leq |\cos wy'/\cos wy| \leq 1.1 \quad \text{Condition (1)}$$

$$0.2 \leq \Phi1/(\Phi2 \cdot f1) \leq 2 \quad \text{Condition (2)}$$

where wy' is the angle at which the chief ray corresponding to the largest half-field angle is incident onto the image pickup surface, wy is the half-field angle of a ray incident onto the image pickup surface;

$\Phi1$ is the diameter of the aperture stop, $\Phi2$ is the maximum outer diameter of the objective optical system, and f1 is the focal length of the front lens group.

When the upper limit of Condition (1) above is not satisfied, the field angle will be too large, resulting in failure to ensure a required scale factor. When the lower limit of Condition (1) above is not satisfied, the angle of incidence onto the image pickup element will be too large, resulting in failure to maintain uniform image qualities (for example, color reproduction and brightness) within the field of view.

It is desirable that the magnifying endoscope has a maximum outer diameter of less than 4 mm in order to insert it into the treatment tool insert channel of a conventional endoscope. Accordingly, it is also desirable that the objective optical system be compact with a maximum outer diameter of less than 2 mm. The small-sized objective optical system having a large scale factor and a high resolution comprises, from the object side, a lens group having positive refractive power and an aperture stop, and desirably satisfies the above Condition (2). The lower limit of Condition (2) prevents the objective optical system from having a larger aperture in association with a larger numerical aperture, i.e., this condition ensures compactness. Thus, when the lower limit of Condition (2) is not satisfied, the objective optical system will have both a larger total length and a larger outer diameter, resulting in it not being compact. When the upper limit of Condition (2) is not satisfied, aberrations are difficult to correct.

In addition, in order to obtain a high contrast along with clear images, the objective optical system needs to have a resolution that is higher than the pixel pitch of the image pickup element and lower than the diffraction limit of the objective optical system. Preferably, the following Condition (3) is satisfied:

$$0.1 \leq |p \cdot NA^2/(0.61 \cdot \lambda \cdot \beta_0)| \leq 0.8 \quad \text{Condition (3)}$$

where p is the pixel size of the image pickup element,

NA is the numerical aperture, $\lambda$ is the wavelength at the e-line (546.1 nm), and $\beta o$ is the image scale factor of the objective optical system.

When the lower limit of Condition (3) is not satisfied, sufficient contrast will not be obtained. When the upper limit of Condition (3) is not satisfied, aberrations become difficult to correct, making it impossible to obtain fine images.

The focus adjustment method for the image pickup unit of the present invention is for an image pickup unit that includes an image pickup element and an objective optical system having an image scale factor with an absolute value greater than unity. The focus adjustment method for the image pickup unit of the present invention preferably includes the following steps, performed in the indicated order:

(a) fixing an object at a specified distance from the object-side leading surface of the objective optical system as the reference position;

(b) moving the image pickup element along the optical axis of the objective optical system to detect at least two image pickup surface positions of the image pickup element at which the object image has a desired (predetermined) contrast value; and (c) obtaining, based on the two image pickup surface positions, the position of the image pickup element at which the object image has the largest contrast.

In addition, the focus adjustment method according to the present invention may preferably further comprise the following step:

(d) detecting the orientation of the object using interference patterns of light reflected by the object-side leading surface of the objective optical system and the object so as to determine the object reference position for focus adjustment.

Furthermore, the step (a) preferably includes a step in which the distance of the position at which the object is placed from the front end surface of the objective optical system is measured within a precision and accuracy smaller than a micron (i.e., in sub-microns) before the object is actually set at such a position. Otherwise, the step (a) preferably includes a step in which an appropriate number of spacer(s), each of which has a thickness set within an accuracy of less than a micron, is placed on the front end surface of the objective optical system in order to determine the position where the object is placed.

The focus adjustment apparatus preferably includes an object supporting part capable of supporting an object at a specified distance from the most object-side surface of the objective optical system, a movable stage having a support member for fixing the image pickup element on the moveable stage, and a data processing unit which calculates the contrast of images formed on the image pickup surface and detects the two positions of the image pickup element at which the object image has the predetermined contrast value and, using these two detected positions, calculates the position of the image pickup surface at which the object image has the largest contrast. The movable stage is movable along the optical axis of the objective optical system at least between two positions where two images formed on the image pickup surface of the image pickup element by the objective optical system have a predetermined contrast value.

The apparatus for determining the range of focus for an image pickup unit of an endoscope includes: a first stage having a support member for supporting the image pickup unit at a fixed position; a second stage having a support member for supporting an object, with the second stage being movable at least between a position where the object contacts the most object-side surface of the objective optical system and a position where an image of the object formed on an image pickup surface of the image pickup element by the objective optical system has a predetermined contrast value; and a detector that is capable of detecting the position of the object along the optical axis.

The method of determining the range of focus for an image pickup unit of an endoscope includes the steps of:

(a) making a contrast chart object come in contact with the object-side surface of the objective optical system;

(b) moving the contrast chart object along the optical axis of the objective optical system until images formed on an image pickup surface of the image pickup element have a predetermined contrast value; and (c) detecting the position of the contrast chart object along the optical axis where the predetermined contrast value is achieved.

An image pickup unit according to the present invention is provided with an image pickup element and an objective optical system that forms a magnified image of an object such that the absolute value of the image scale factor is greater than unity. The focus of the objective optical system is adjusted using the method described previously.

A conventional endoscope having a wide field of view is used for thorough examination of tissues in the body (i.e., so that no tissues are overlooked). For a region that is difficult to diagnose from a tissue image, such as a minute lesion, the image pickup unit of the present invention is inserted as a magnifying endoscope into the body through the treatment tool insert channel of a conventional endoscope to examine cellular structures in a given region.

The images observed by conventional endoscopes of parenchyma tissue under epithelial cells look reddish. Epithelial cells that are observed through a magnifying endoscope are transparent and of low contrast, making them difficult to see using conventional endoscopes.

Therefore, coloring agents are often used prior to examining epithelial cells through a magnifying endoscope. This process uses the difference in time required for the cell nuclei, cell wall, and other components to excrete the coloring agent. This results in improving the contrast with which these different cell components may be viewed using a magnifying endoscope, the tip of which is guided to the region in question and makes contact with the object while observations using a conventional endoscope are continued. A tissue image from the conventional endoscope and a cell image from the magnifying endoscope are then both simultaneously displayed on a TV monitor.

For in vivo cellular observation, the objective optical system should meet requirements such as a large image scale factor, a high image resolution, and a small-size.

First, the scale factor required for visualizing fine cellular structures will be discussed. If bm is the observation scale factor when viewing the monitor, then:

$$bm = bo \cdot bd \qquad \text{Equation (A)}$$

where bo is the image scale factor of the objective optical system, which is the scale factor at which the image of an object is formed on the image pickup element, and bd is the scale factor of the display, namely, the monitor display screen size divided by the image pickup surface size of the image pickup element.

Conventional endoscopes realize an observation scale factor of 30 to 50 when using a 14 inch monitor. Zoom optical systems having a magnifying function realize an observation scale factor of approximately 70. An observation scale factor of approximately 200 to 2000 is necessary for cellular observation. Therefore, it is desired that the observation optical system satisfies both Condition (1) above and the following Condition (4):

$$1 < |\beta o| \leq 10 \qquad \text{Condition (4)}$$

where

βo is the image scale factor of the objective optical system.

Diseased tissues can be identified with a resolution of millimeters or sub-millimeters. However, cellular observation requires a resolution of microns or sub-microns. In order to form detailed images of a transparent object that provides only a small difference in refractive index as well as a low contrast, the interference of light diffracted from the object may be advantageously utilized in order to amplify the contrast. When the interference of diffracted light is utilized, the objective optical system needs to have a larger numerical aperture NA in order to collect higher diffraction orders of the diffracted light and, preferably, satisfies the following Condition (5):

$$0.1 \leq NA \leq 0.8 \qquad \text{Condition (5)}$$

To prevent excessive curvature of field, it is desirable that the objective optical system be formed of, in order from the object side, a front lens group having positive refractive power, an aperture stop, and a rear lens group having positive refractive power. In addition, the following Condition (6) is preferably satisfied in order to achieve both compactness and a large image scale factor:

$$2 \leq f2/f1 \leq 10 \qquad \text{Condition (6)}$$

where f2 is the focal length of the rear lens group, and f1 is the focal length of the front lens group.

If the lower limit of Condition (6) is not satisfied, the required image scale factor will not be achieved. If the upper limit of Condition (6) is not satisfied, a larger overall length and a larger outer diameter will result; thus, compactness will not be achieved.

Figure 2:
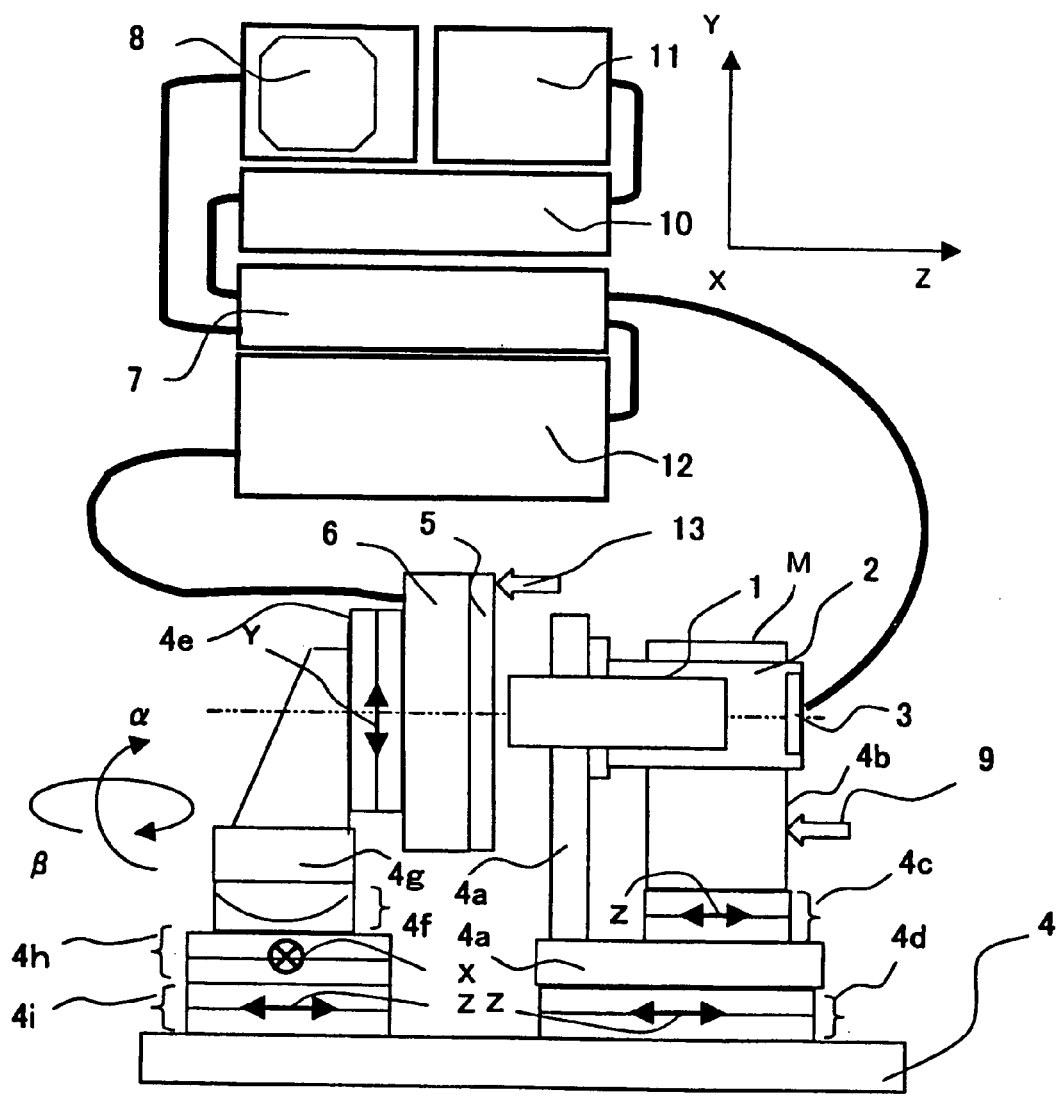
FIG. 2 shows an example of one configuration of the focus adjustment apparatus according to the present invention.

One example of a focus adjustment apparatus, which also works as a focus range determination apparatus, will now be described with reference to FIG. 2. In the figure, M is the image pickup unit that is formed of an image sensor unit 2 having an image pickup element 3 and an objective optical system 1. The structure of the image pickup unit M will be explained in detail later. Reference numeral 4 denotes a base of the apparatus. The base 4 has support members 4a and 4b that support the image pickup unit M, a Z-stage 4c on which the support member 4b is mounted for moving the support member 4b in the Z direction relative to the support member 4a, and a Z-stage 4d on which the support member 4a is mounted for moving the support member 4a in the Z direction relative to the support base 4. Further, there are provided: a Y-stage 4e on which an illumination unit 6 is mounted for moving the illumination unit 6 in the Y direction relative to the base 4; an α goniometer stage 4f and a β goniometer stage 4g which rotate the Y-stage 4e in the α direction and in the β direction, respectively; an X-stage 4h that moves the α goniometer stage and the β goniometer stage in the X direction relative to the base 4; and a Z-stage 4i that moves the X-stage 4h in the Z direction. The Z direction and the Y direction are shown in the figure, and the X direction is a direction perpendicular to the plane of the figure.

The image pickup unit M is held so that the objective optical unit 1 is supported by the support member 4a, the image sensor unit 2 is supported by the support member 4b and each of which can move and stop along Z the direction for focus adjustment. A micro-sensor 9 obtains the positional information of the image pickup element in sub-microns.

An object 5 used for focus adjustment is illuminated by an illumination unit 6 from the back, and fixed to the base 4 in a manner so that it can be adjusted and fixed relative to the objective optical system 1 in the directions XYZ, α and β

The illumination unit 6 is supplied with illumination light by a light source 12. An object image projected on the image pickup element 3 is signally transformed and transferred to an image signal processing unit 7 where it is transformed into image signals, which are then displayed on a monitor 8. The image signal processing unit 7 and light source 12 cooperate to control the amount of light for optimum brightness. An arithmetic processing unit 10 calculates the contrast value of the image signals and gives the result on a monitor 11.

A method for detecting the contrast is shown in FIGS. 3(a) and 3(b). When a transparent sample having an alternate black/white band pattern shown in FIG. 3(a) is used as an object, an image signal as shown in FIG. 3(b) is obtained. The figure shows, with the brightness as ordinate and the scanning direction as abscissa, the image signal waveform obtained after spatial brightness signals obtained during the imaging are time-averaged. In this instance, assuming that Imax and Imin are the maximum and minimum, respectively, of the detected waveform corresponding to the black/white of the object, the contrast I is defined as follows:

$$I = (Imax - Imin)/(Imax + Imin) \quad \text{Equation (B)}$$

Figure 4:
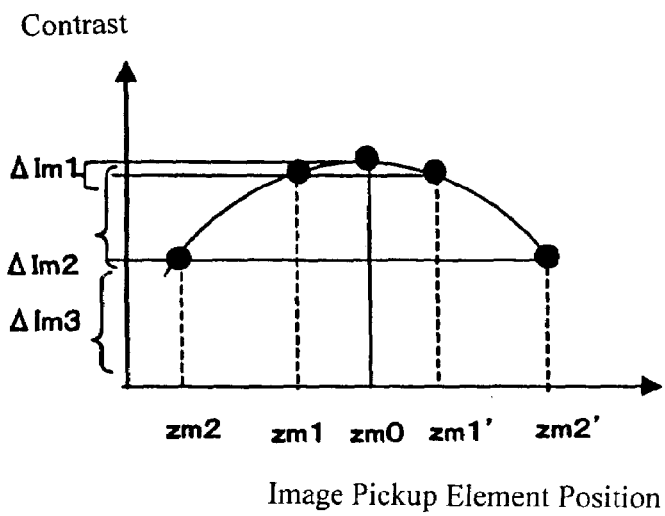
FIG. 4 is a graphical representation in which the contrast obtained by the method illustrated in FIGS. 3(a) and 3(b) is plotted for various axial positions of the image pickup surface of the image pickup element, with the image pickup element being in-focus at the position zm0.

FIG. 4 is a graphical representation in which the contrast (as defined in Equation (B) above) that is obtained by the method in FIGS. 3(a) and 3(b) is plotted on the ordinate as a function of the image pickup element position. Determining the optimum image position zm0 (i.e., the maximum contrast) by detecting a contrast variation amount $\Delta$Im1, and then measuring the mean of the positions along the abscissa of the points Zm1 and Zm1' is difficult, since the variation in contrast $\Delta$Im1 is small for a given change in abscissa position. Therefore, the points Zm1 and Zm1' are difficult to detect with accuracy, leading to errors in computing the optimum position zm0.

However, if the optimum image position zm0 is instead determined by detecting a contrast variation $\Delta$Im2 by determining the mean of the points zm2 and zm2', the optimum image position zm0 may be calculated with increased accuracy, since the variation in contrast is higher at the points zm2, zm2' for a given change in the image pickup element position. For example, if $\Delta$Im2 is increased, the positions zm2 and zm2' may be detected with higher accuracy. If the $\Delta$Im3 is about 20% (which means the contrast value at the position zm2 and zm2' is about 0.2 by using Equation B), the contrast variation $\Delta$Im2 will become large enough to determine the position zm0 with sufficient accuracy. An optical system that is favorably corrected for spherical aberration has a contrast curve that is symmetric on both sides of the in-focus position. Thus, in an optical system that is favorably corrected for spherical aberration, the contrast peak may be accurately determined by calculating the middle point between the positions zm2 and zm2', thereby determining the optimum-focus image position zm0.

For an optical system in which the influence of spherical aberration can not be ignored, the contrast peak will not coincide with the middle point between zm2 and zm2', but instead will be shifted forward or backward from the middle point. In an optical system having an image scale factor with an absolute value greater than unity, such as in the image pickup unit of the present invention, an error on the object side (i.e., the positional deviation between the optimum focus position and the actual position of the image pickup surface of the image pickup device) is projected by the objective optical system onto the image side such that the error is reduced. Thus, resolution within the depth of field of the objective optical system will not be significantly degraded. If necessary, the depth of field can be evaluated and appropriately corrected, described later.

Two embodiments of the magnifying image pickup unit of the present invention will now be described in detail.

Embodiment 1

The structure of Embodiment 1 will now be described with reference to FIG. 7(a). The image pickup unit is formed of an objective unit 101 having a uniform diameter within an objective frame 102 and an image sensor unit. The objective unit 101 consists of, in order from the object side, a first lens group G1 having positive refractive power, an aperture stop 103, and a second lens group G2 having positive refractive power. An image pickup element 105 is fixed to an image pickup frame 106 via a cover glass 104, forming an image sensor unit.

The image pickup unit is focused by changing the distance 107 between the objective optical system and the image pickup element. The insert section for the magnifying endoscope is constructed of a hard tip member 108 and an outer sheath member 110. The image pickup unit is fixed in the insert section via an intermediate member 109.

Figure 7A:
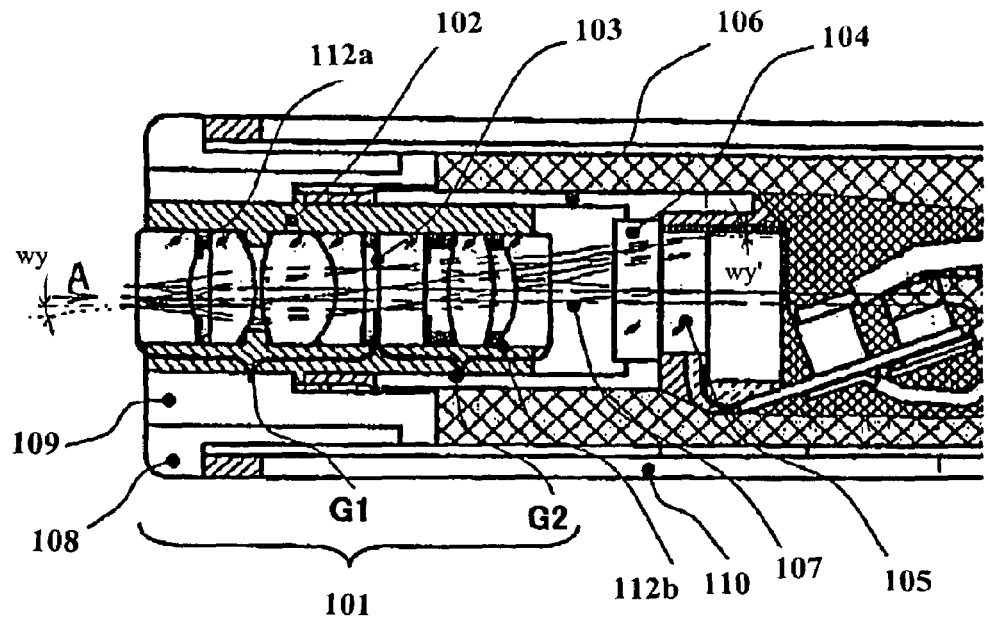
FIGS. 7(a)–7(c) show the endoscope image pickup unit according to Embodiment 1 of the present invention, with FIG. 7(a) being a length cross section, with FIG. 7(b) being an end view as viewed in the direction indicated by the arrow A in FIG. 7(a), and with FIG. 7(c) being an enlarged view of the lens portion of FIG. 7(a).
Figure 7B:
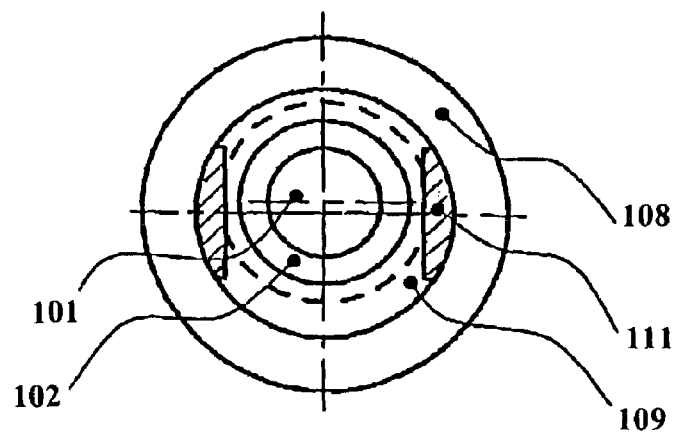
Figure 7C:
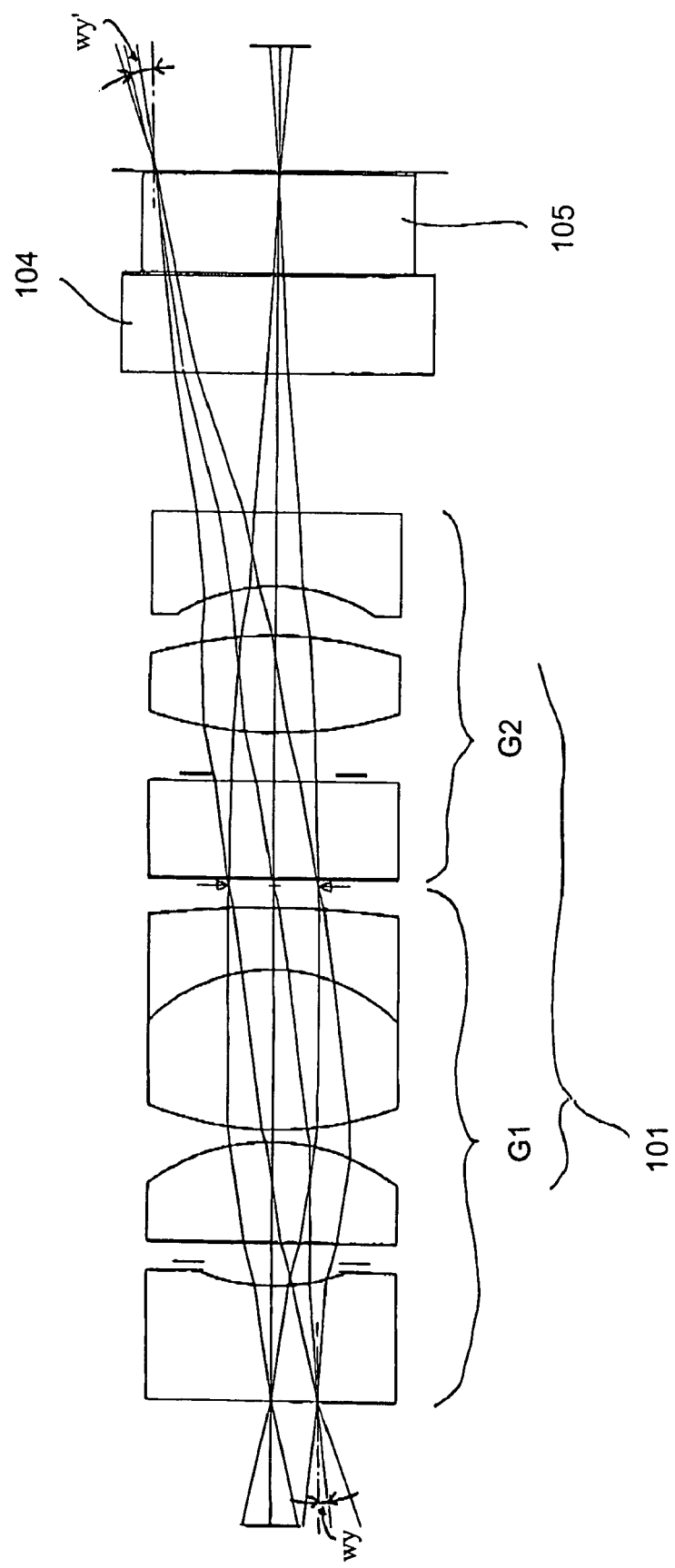

FIG. 7(b) is a cross section as viewed in the direction indicated by the arrow A in FIG. 7(a). The intermediate member 109 has cutouts (shaded parts) on the perimeter, through which an illumination fiber 111 is inserted and fixed. After the intermediate member 109 and illumination fiber 111 are fixed to the hard tip member 108, the image pickup unit is inserted and fixed.

When adjustment is required, for example in the image scale factor, gap adjustment members 112a and 112b provided before and after the aperture stop can be used for more or less space, if necessary. A gap adjustment ring made of ultra-thin plates is used for gap adjustment. A gap adjustment member is formed of a stack of ultra-thin plates. A different number of ultra-thin plates is used during assembly in order to set the gap to a suitable value according to the dimensional tolerance of parts actually used.

Table 1 below lists the surface number #, in order from the object side, the radius of curvature R (in mm) of each surface, the on-axis spacing D (in mm) between surfaces, as well as the refractive index $N_d$ and the Abbe number $v_d$ (both measured at the d-line ($\lambda$=587.6 nm)), and the lens outer diameter (in mm) for each optical surface of the image pickup unit of Embodiment 1.

TABLE 1

| # | R | D | $N_d$ | $v_d$ | Lens Outer Diameter |
|---|---|---|---|---|---|
| 1 | ∞ | 0.46 | 1.5183 | 64.14 | 1 |
| 2 | 0.84 | 0.17 | 1 | | |
| 3 | ∞ | 0.4 | 1.7323 | 54.68 | 1 |
| 4 | −0.817 | 0.05 | 1 | | |
| 5 | 1.353 | 0.65 | 1.7323 | 54.68 | 1 |
| 6 | −0.703 | 0.25 | 1.7044 | 30.131 | |
| 7 | −3.804 | 0.09 | 1 | | |
| 8 | ∞ (stop) | 0.03 | 1 | | |
| 9 | ∞ | 0.4 | 1.5156 | 75.00 | 1 |
| 10 | ∞ | 0.2 | 1 | | |
| 11 | 1.566 | 0.4 | 1.67 | 48.32 | 1 |
| 12 | −1.566 | 0.2 | 1 | | |
| 13 | −0.729 | 0.3 | 1.5198 | 52.43 | 1 |
| 14 | ∞ | 0.56 | 1 | | |
| 15 | ∞ | 0.4 | 1.5183 | 64.14 | |
| 16 | ∞ | 0.01 | 1.5119 | 63.00 | |
| 17 | ∞ | 0.4 | 1.6138 | 50.20 | |

TABLE 1-continued

| # | R | D | $N_d$ | $v_d$ | Lens Outer Diameter |
|---|---|---|---|---|---|
| 18 | ∞ | 0.01 | 1.5220 | 63.00 | |
| 19 | ∞ | 0 | | | |

Distance to object = 0
Image height = 0.500

Embodiment 2

Figure 8A:
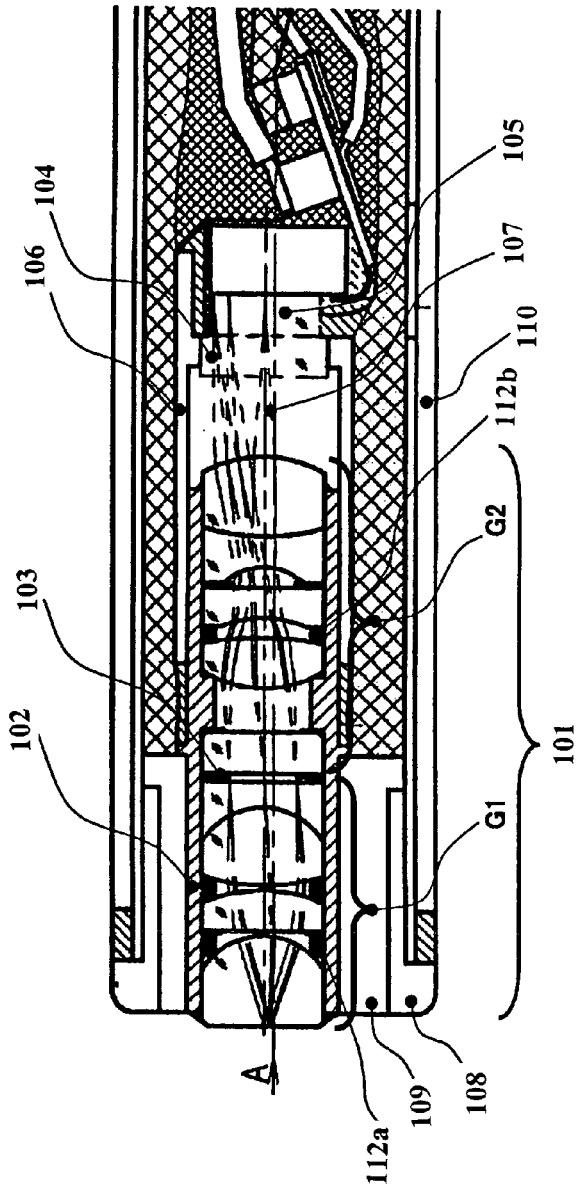
FIGS. 8(a) and 8(b) show the endoscope image pickup unit according to Embodiment 2 of the present invention, with FIG. 8(a) being a length cross section and FIG. 8(b) being an end view as viewed in the direction indicated by the arrow A in FIG. 8(a)
Figure 8B:
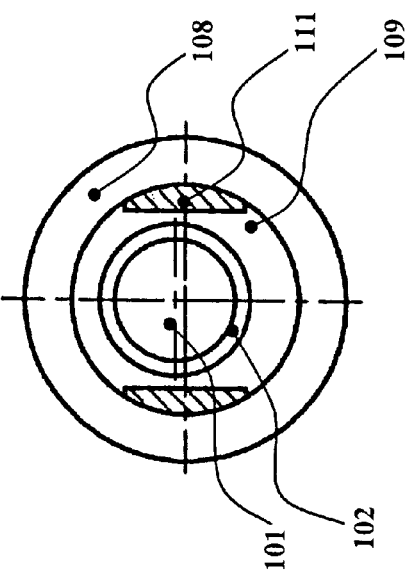

FIGS. 8(*a*) and 8(*b*) show the structure of Embodiment 2. The same reference numbers are used for identical components as in Embodiment 1, and thus further discussion of these components will be omitted.

Table 2 below lists the surface number #, in order from the object side, the radius of curvature R (in mm) of each surface, the on-axis spacing D (in mm) between surfaces, as well as the refractive index $N_d$ and the Abbe number $v_d$ (both measured at the d-line (λ=587.6 nm)), and the lens outer diameter (in mm) for each optical surface of the image pickup unit of Embodiment 2.

TABLE 2

| # | R | D | $N_d$ | $v_d$ | Lens Outer Diameter |
|---|---|---|---|---|---|
| 1 | ∞ | 0.88 | 1.8882 | 40.76 | 1.2 |
| 2 | −0.703 | 0.05 | 1 | | |
| 3 | ∞ | 0.4 | 1.5183 | 64.14 | 1.2 |
| 4 | −1.485 | 0.05 | 1 | | |
| 5 | 2.085 | 0.76 | 1.8081 | 46.57 | 1.2 |
| 6 | −0.703 | 0.25 | 1.8126 | 25.42 | 1.2 |
| 7 | ∞ | 0.05 | 1 | | |
| 8 | ∞ (stop) | 0.03 | 1 | | |
| 9 | ∞ | 0.4 | 1.5156 | 75.00 | 1.2 |
| 10 | ∞ | 0.43 | 1 | | |
| 11 | 1.131 | 0.5 | 1.8395 | 42.72 | 1.2 |
| 12 | −3.127 | 0.2 | 1 | | |
| 13 | −1.061 | 0.3 | 1.8126 | 25.42 | 1.2 |
| 14 | ∞ | 0.2 | | | |
| 15 | −0.592 | 0.3 | 1.8081 | 46.57 | 1.2 |
| 16 | 2.132 | 0.77 | 1.8126 | 25.42 | 1.2 |
| 17 | −1.262 | 0.77 | 1 | | |
| 18 | ∞ | 0.4 | 1.5183 | 64.14 | |
| 19 | ∞ | 0.01 | 1.5119 | 63.00 | |
| 20 | ∞ | 0.4 | 1.6138 | 50.20 | |
| 21 | ∞ | 0.01 | 1.5220 | 63.00 | |
| 22 | ∞ | 0 | 1 | | |

Distance to object = 0
Image height = 0.500

Table 3 below lists technical data regarding Embodiments 1 and 2.

TABLE 3

| item | legend | unit | Embodiment 1 | Embodiment 2 |
|---|---|---|---|---|
| Image scale factor | βo | | −2.678847 | −6.63 |
| Focal length of front lens group | f1 | mm | 0.765 | 0.591 |
| Focal length of rear lens group | f2 | mm | 3.476 | 4.557 |
| Focal length | f | mm | 0.657 | 0.797 |
| Half-field angle | wy | deg | 6.141 | 3.95 |
| Exit angle of main ray | wy' | deg | 13.965 | 6.02 |
| Numerical aperture on object side | NA | | 0.2184 | 0.55 |
| Stop diameter | Φ1 | mm | 0.36 | 0.66 |

TABLE 3-continued

| item | legend | unit | Embodiment 1 | Embodiment 2 |
|---|---|---|---|---|
| Maximum lens diameter | Φ2 | mm | 1 | 1.2 |
| Pitch | p | μm | 4 | 4 |
| Reference wavelength | λ | μm | 0.546 | 0.546 |

Table 4 below lists the Conditions 1–6, as well as the values obtained for these conditions by Embodiments 1 and 2.

TABLE 4

| Condition No. | Condition | Embodiment 1 | Embodiment 2 |
|---|---|---|---|
| 1 | $0.9 \leq |\cos wy'/\cos wy| \leq 1.1$ | 0.976 | 0.997 |
| 2 | $0.2 \leq \Phi1/(\Phi2 \cdot f1) \leq 2$ | 0.471 | 0.931 |
| 3 | $0.1 \leq |p \cdot NA^2/(0.61 \cdot \lambda \cdot \beta_0)| \leq 0.8$ | 0.215 | 0.544 |
| 4 | $1 < |\beta o| \leq 10$ | 2.680 | 6.630 |
| 5 | $0.1 \leq NA \leq 0.8$ | 0.220 | 0.550 |
| 6 | $2 \leq f2/f1 \leq 10$ | 4.544 | 7.711 |

The method as described above enables focus adjustment in which the optimum image position is detected for an object placed at a specified distance. After focus adjustment it is required that the depth of field of the objective optical system of the image pickup unit be evaluated and the distance at which an object is placed for the focus adjustment be verified. This can be performed as follows.

Figure 5:
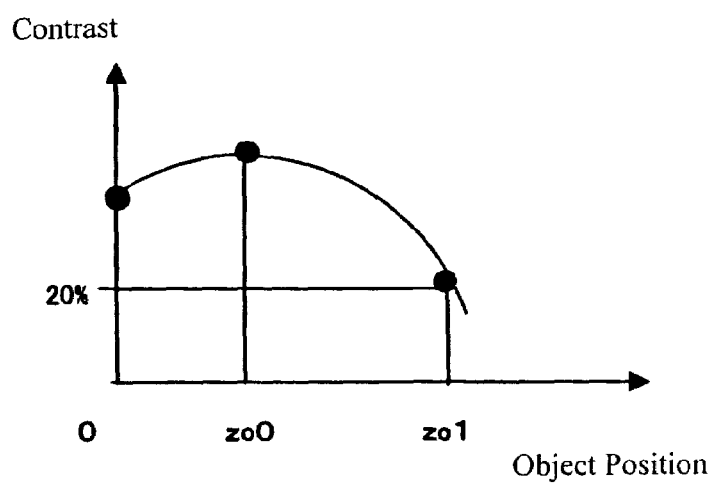
FIG. 5 shows the variation in contrast relative to the object distance in the situation where the contrast is not balanced on each side of the in-focus position.

FIG. 5 shows the contrast variation relative to the object position. In FIG. 5, the contrast values are plotted for various object distances after the image pickup surface of the image pickup element is fixed for being in-focus. The contrast is at a peak at zo0 where an object is placed for focus adjustment and decreases as the object moves away from this point. In the figure, the distant 0 means that the object and object-side leading surface of the objective optical system of the image pickup unit are in contact and used as the reference position for detecting the object distance.

With the lower tolerance limit of observable contrast being set for a predetermined value, such as 20%, the object distance at which the lower limit is found is detected to obtain the depth of field range of the objective optical system of the image pickup unit after the focus adjustment. In FIG. 5, the depth of field ranges from 0 to zo1.

Figure 6:
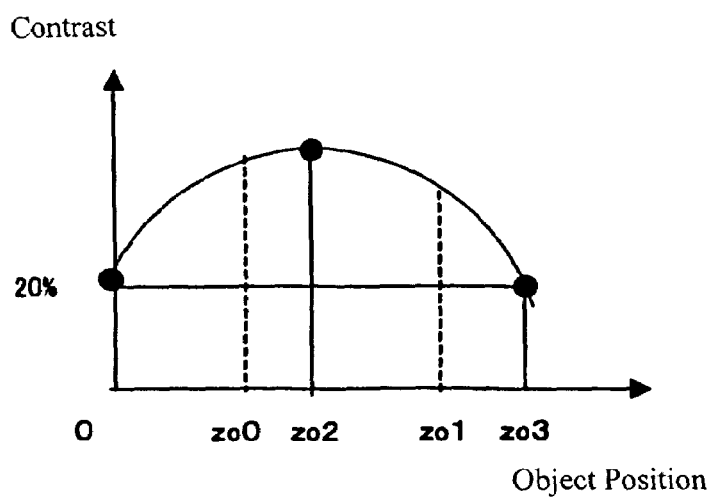
FIG. 6 shows the variation in contrast relative to the object distance in the situation where a more balanced focus adjustment is obtained on each side of the in-focus position.

The method outlined above is used to verify the focus position. If, following a depth of field verification, the focus range up to zo1 is insufficient and the contrast at the contact position 0 is above the lower tolerance limit of 20%, the object is moved to the point zo2 that is farther away from the object-side leading surface of the objective optical system than is the object position zo0 used for the first focus adjustment. Then, the focus adjustment is repeated to obtain the contrast curve shown in FIG. 6. In FIG. 6, the objective optical system has a larger depth of field between 0 and zo3. The object position for focus adjustment is verified and adjusted so that the optimum depth of field is obtained using the method described above.

In addition, if necessary, focus and depth of field are further adjusted by observing an image actually obtained by the image pickup unit. This is because the quality of the image depends on, ultimately, the visual sense of a human being. Therefore, it is preferable, in some case, to take into account the human sense in addition to the adjustment by using an adjustment apparatus, such as described above.

In order to conduct this method, a way to accurately detect the object position is required. The focus adjustment and the focus range check apparatus shown in FIG. 2 is equipped with a micro-sensor 13, either a contact or a non-contact type, in order to accurately detect the object position. The micro-sensor detects the position in sub-microns. It is preferred that an operation circuit be provided for calculating and removing the mechanical error associated with the fixing and moving of the object so as to measure the position of the moving object with accuracy. A micro-stage or stepping motor can be used for moving the object if it can be moved in steps that are measured in sub-microns.

When the object-side leading surface of the objective optical system of the image pickup unit is used as the reference position for obtaining the object distance, it is necessary to accurately detect the contact between the object and leading surface of the objective optical system.

With the focus adjustment and the focus range check apparatus of the present invention, the object may be deformed or inclined relative to the objective optical system if it is further pressed after contacting the object-side leading surface of the objective optical system. In images observed after the object starts moving toward the leading surface of the objective optical system, the object seems to move in an orthogonal direction once contact is made with the leading surface. In other words, the object seems to move upward/downward or to the right/left relative to the center of the field of view as soon as it starts deforming or inclining. Detecting such orthogonal movement of at least a portion of the image of the object results in detecting the point of contact between the object and the leading surface of the objective optical system.

The objective optical system used in the image pickup unit of the present invention projects slight inclinations of the object relative to the objective optical system onto the image side in an enlarged size. Thus, the focus adjustment and focus range check apparatus are provided with a mechanism for detecting the object orientation and correcting it, if necessary.

For example, the objective optical system of the present invention has a very small depth of field and the object and the object-side leading surface of the objective optical system are very near one another. Thus, interference fringes that occur between the object and the object-side leading surface of the objective optical system when the object lies in a proper orientation can be used for detecting the orientation of the object. An interference pattern that has been previously recorded is compared with that of the moving object in order to detect proper object orientation. In this way, the object is always maintained in a proper orientation while the focus adjustment is repeated, and the focus adjustment is performed with excellent reproducibility. As another way to detect the object orientation, a collimator can be used.

The object inclination relative to the objective optical system can be adjusted by providing goniometer stages 4f and 4g, for example, on the part holding the object.

The method described above improves reproducibility and focus adjustment accuracy compared with the conventional focus adjustment method in which an object is placed at plural distances.

When the objective optical system of the present invention has a very small depth of field and the object and the object-side leading surface of the objective optical system are very near one-another, the measurement from the reference position can be omitted. For example, if the object should be placed at a distance of several micrometers from the reference position, a transparent film having a thickness determined within an accuracy of a sub-micron may be formed on the object surface by, for example, a deposition process and then the object may be made to contact the reference surface. In this way, the object may be placed at a desired distance with accuracy. Because the thickness of a transparent film can be controlled accurately (within nanometers), such a procedure provides sufficient accuracy for determination of the distance between the object and the reference surface.

If the object should be positioned at a distance of several tens of micrometers from the reference position, a thin plate having a thickness that is accurately determined within micrometers may be inserted between the object and the reference surface. In this way, the object may be positioned at a desired distance from the object-side leading surface with accuracy. An etching process for manufacturing semiconductors, for example, can be used to control the thickness of the thin plate with an accuracy within micrometers. Each of these techniques provides sufficient accuracy for determining the distance between the object and the reference surface. In this way, a single element may be used to ensure a proper distance between the object and the reference surface, thus improving reproducibility of the focus adjustment.

When a transparent sample having an alternate black/white band pattern as shown in FIG. 3(a) is used as the object for focus adjustment, the band should have a width of sub-microns. A desired pattern applied on a glass substrate using an etching process for manufacturing semiconductors or a diffraction grating also may be used.

Figure 9:
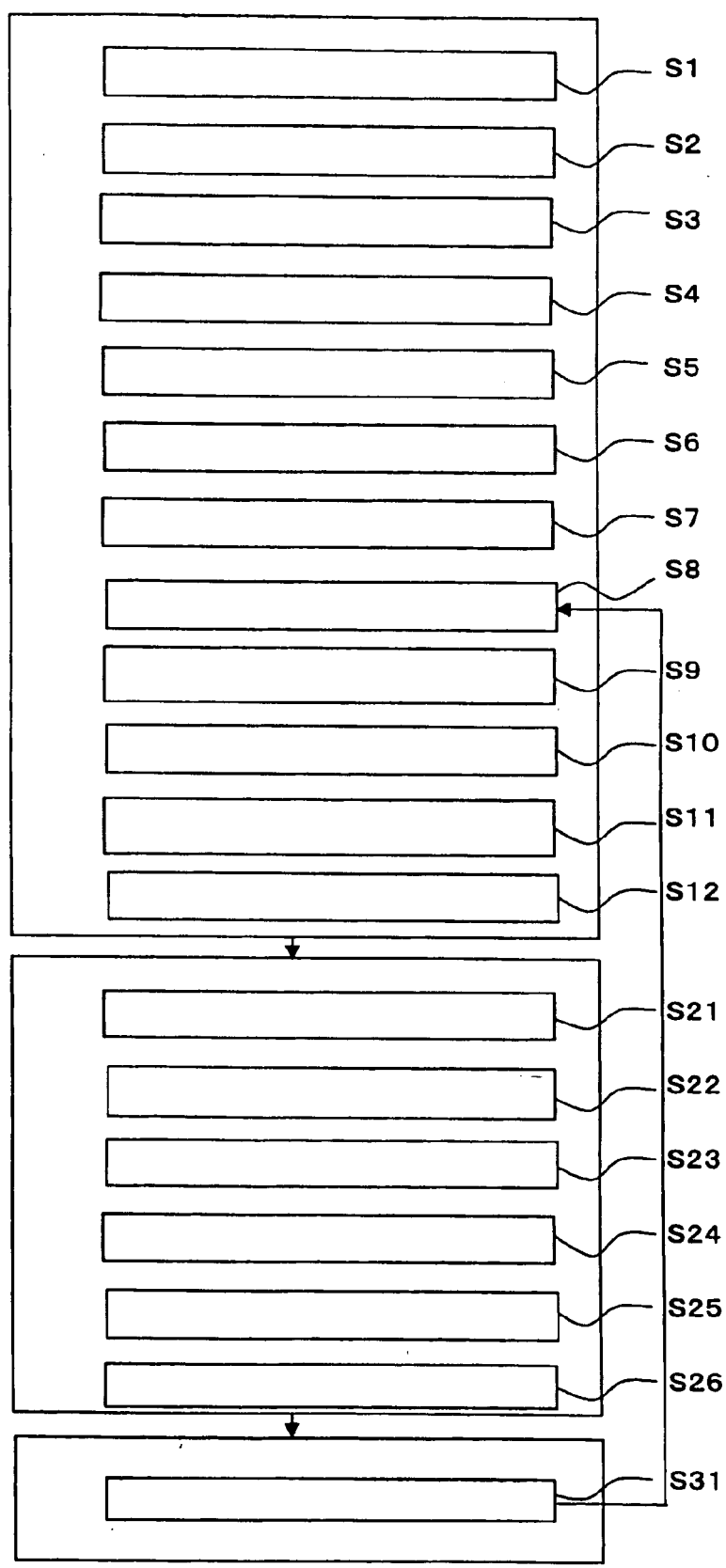
FIG. 9 is a flow chart of the focus adjustment method (steps S1 through S12), the focus range determining method (steps S21 through S26), and the focus correction (step S31).

FIG. 9 is a flow chart of the focus adjustment method and the focus range check method of the present invention.

The focus adjustment method includes the steps S1 through S12, as follows:

step S1—insert the objective optical system 1 until it contacts the image sensor unit 2;

step S2—adjust the inclination between both the objective optical system 1 and the image sensor unit 2 and fix them to the support member 4a and 4b with a jig;

step S3—attach the object to the illumination unit 6 and make the object contact the object-side leading surface of the objective optical system by moving the object with the Z-stage 4i;

step S4—move the image sensor unit 2 with the Z-stage 4c until the object as imaged by the objective optical system is in-focus, while observing the image and also observing the calculated contrast value by the processor 7, both of which are displayed on the monitors 8 and 11;

step S5—detect the contact distance between the object 5 and the objective optical system 1 by the micro-sensor 9, or the contact distance and inclination between the object 5 and the objective optical system 1 by detecting the interference pattern;

step S6—correct (i.e., adjust) the distance to the object as well as the inclination of the object by using the X-stage 4h, Y-stage 4e, Z-stage 4i, and the goniometer stages 4f and 4g so that the interference pattern becomes a desired state;

step S7—set the position of the object as a reference position (origin point) for adjustment in which the object just begins to contact the leading surface of the objective optical system and memorize the position using the processor 7;

step S8—move the object to a position apart from the reference position by a predetermined distance with the Z-stage 4i;

step S9—move the image sensor unit 2 away from the contact point with the objective optical system 1 with the Z-stage 4*c*;

step S10—detect the contrast that corresponds to the image sensor unit position;

step S11—obtain the best focus position using the two image pickup surface positions where a desired contrast is achieved; and step S12—move the image sensor unit 2 to the best focus position with the Z-stage 4*c*.

The focus range check method includes the steps S21 through S26, as follows:

step S21—move the object 5 to the object-side leading surface of the objective optical system 1 (i.e., the origin point) with the Z-stage 4*i*;

step S22—move the object 5 from the object-side leading surface of the objective optical system 1 with the Z-stage 4*i* while the object position is detected, with the contrast that corresponds to the object position being displayed on the monitor;

step S23—stop moving the object at the position where the contrast has the lower limit value;

step S24—obtain the focus range from the object position;

step S25—verify the focus range; and step S26—fix and end the process if the focus range is satisfactory.

Focus correction consists of a single step, namely:

step S31—correct the distance at which the object 5 is placed with the Z-stage 4*i*.

Following the focus correction step S31, the steps S8–S12, S21–S26 are repeated. If the focus is still unsatisfactory, the flow loops again back to the step S8 and the steps S8–S12, S21–S26, and S31 are repeated.

The structure and method described above enable a high resolution, magnifying endoscope to be realized with an imaging system having a compact design and a large scale factor. Further, it enables the high resolution, magnifying endoscope to be focused accurately with an optimum depth of field, which allows for in vivo real-time observation of living cells.

The invention being thus described, it will be obvious that the same may be varied in many ways. Such variations are not to be regarded as a departure from the spirit and scope of the invention. Rather, the scope of the invention shall be defined as set forth in the following claims and their legal equivalents. All such modifications as would be obvious to one skilled in the art are intended to be included within the scope of the following claims.

What is claimed is:

1. An image pickup unit for picking up magnified images of an object, comprising:

an objective optical system having an image scale factor with an absolute value greater than unity and an image pickup surface, wherein the objective optical system includes, in order from the object side, a front lens unit having positive refractive power and an aperture stop having an opening, and the objective optical system satisfies the following conditions $$0.9 \leq |\cos wy'/\cos wy| \leq 1.1$$

$$0.2 \leq \Phi 1/(\Phi 2 \cdot f1) \leq 2$$

where $wy'$ is the angle at which the chief ray corresponding to the largest half-field angle is incident onto the image pickup surface, $wy$ is the half-field angle of a ray incident onto the image pickup surface, $\Phi 1$ is the diameter of the opening of the aperture stop, $\Phi 2$ is the largest outer diameter of the objective optical system, and $f1$ is the focal length of the front lens unit.

2. The image pickup unit according to claim 1, wherein:

the objective optical system comprises, in order from the object side, the front lens unit, the aperture stop, and a rear lens unit having positive refractive power, and the following condition is satisfied $$2 \leq f2/f1 \leq 10$$

where $f2$ is the focal length of the rear lens unit, and $f1$ is the focal length of the front lens unit.

* * * * *